United States Patent
Garito et al.

[11] Patent Number: 5,984,918
[45] Date of Patent: *Nov. 16, 1999

[54] ELECTROSURGICAL HANDPIECE WITH MULTIPLE ELECTRODE COLLET

[76] Inventors: Jon C. Garito; Alan G. Ellman, both of 1135 Railroad Ave., Hewlett, N.Y. 11557

[*] Notice: This patent is subject to a terminal disclaimer.

[21] Appl. No.: 08/995,620

[22] Filed: Dec. 22, 1997

[51] Int. Cl.[6] .................................................. A61B 17/39
[52] U.S. Cl. .................. 606/41; 606/45; 606/49
[58] Field of Search .................... 606/37–52, 1, 606/14–16

[56] References Cited

U.S. PATENT DOCUMENTS

| | | | |
|---|---|---|---|
| 3,746,814 | 7/1973 | Lackey et al. | 200/505 |
| 3,875,945 | 4/1975 | Friedman | 606/45 |
| 3,920,022 | 11/1975 | Pastor | 606/41 |
| 3,961,630 | 6/1976 | Gonser | 606/41 |
| 4,638,802 | 1/1987 | Okada | 606/47 |
| 4,657,016 | 4/1987 | Garito et al. | 606/45 |
| 4,711,239 | 12/1987 | Sorochenko et al. | 606/48 |
| 5,125,058 | 6/1992 | Tenerz et al. | 385/66 |
| 5,630,812 | 5/1997 | Ellman et al. . | |

*Primary Examiner*—Lee Cohen
*Assistant Examiner*—David Ruddy

[57] ABSTRACT

An electrosurgical handpiece comprises a handle and a nose piece for threaded engagement with the handle, together with a collet member which cooperates with the handle and nose piece for removably receiving and locking multiple-sized electrosurgical electrodes to the handle. To simplify assembly, the collet end is press-fitted into a bore in the handle. For this purpose, the collet must be constituted of an electrically conductive metal that also has sufficient elasticity that it will tend to return to its unstressed condition. Preferably, the press-fitted collet end is provided with knurls or grooves to ease the press-fitting operation and prevent collet movement with respect to the handle. Preferably, the collet front end is provided with spaced jaws surrounding a single coaxial bore that is able to accommodate two-different sized shanks of electrosurgical electrodes.

18 Claims, 3 Drawing Sheets

ELECTROSURGICAL HANDPIECE WITH MULTIPLE ELECTRODE COLLET

This invention relates to a novel electrosurgical handpiece for receiving an electrosurgical electrode for use in electrosurgical medical, dental, and veterinarian procedures.

BACKGROUND OF THE INVENTION

Electrosurgery is a common procedure for dentists, doctors, and veternarians. Electrosurgical unipolar handpieces are commercially available that will accommodate a wide variety of electrode shapes and sizes, such as needles, blades, scalpels, balls and wire loops. The conventional unipolar handpiece, such as that available from Ellman International, Inc. of Hewlett, N.Y., comprises an elongated electrically-insulating handle with a central bore and having at a first end an externally threaded part for threadingly engaging an internal thread on an electrically-insulating nose piece also fitted with a central bore. A generally cylindrical metal collet seats in the handle bore at the first end and a collet front portion projects forward from the handle. The collet comprises at its front portion flexible jaws formed by a tapered slitted front with a bore sized to receive the shaft or shank of a conventional electrosurgical electrode, and the nose piece has on its interior a matching tapered portion configured such that, when the nose piece is rotated clockwise (CW) while threadingly engaged to the handle, its tapered interior surface engages and gradually closes down the collet jaws so that the electrode, when inserted into the collet bore, is tightly held by the metal collet and a good electrical connection is made to the collet. The back end of the collet is connected to a wire which connects to a conventional electrosurgical instrument supplying electrosurgical currents which, when activated, via a switch on the handpiece or a foot switch or a switch on the instrument, supplies electrosurgical currents to the collet and via the collet to the electrosurgical electrode. When the dentist or doctor desires to change the shape, size or length of the electrode, it is necessary to loosen the nose piece to unlock the collet, remove the existing electrode, and substitute a new electrode.

Reference is made to commonly owned U.S. Pat. No. 5,630,812 which describes a handpiece of the type described above provided with a built-in structure which locks the nosepiece to the handle preventing accidental detachment, the contents of which are herein incorporated by reference.

These types of known handpieces can cause certain difficulties. These difficulties include that the collet can only accommodate a single sized electrode shank. However, the most common electrodes come in two standard-sized shanks, 1/16 or 3/32 inches. Hence, when the surgeon desires to change electrodes, and the new electrode has a different sized shank from the previous electrode, the surgeon must remove the nosepiece during the procedure, remove the collet for the previous electrode and replace with a new collet that can accommodate the shank of the new electrode. This is cumbersome and time consuming, and has the further disadvantage in that it involves a certain effort to remove the nosepiece from the handpiece when the nosepiece makes use of the locking feature described and claimed in the referenced patent.

Another disadvantage of the known handpieces derive from their fabrication or assembly procedure during manufacture of the handpiece. The metal collet, typically of brass so as to be electrically conductive, must be fixed to the handle, typically of an insulating plastic such as Delrin, so that it does not turn or move during the surgical procedure. This is currently accomplished by gluing the back end of the collet, after the electrical cable has been soldered to it, into the bore at the front end of the handle. The gluing step, which takes at least several hours due to the dissimilar materials, requires that the glued parts remain immobile while the glue dries and permanently sets. This significantly slows the assembly procedure and increases the manufacturing cost.

SUMMARY OF THE INVENTION

An object of the invention is an electrosurgical handpiece that can accommodate various shapes and sizes of electrodes while still allowing the nose piece to rotate sufficiently to lock and unlock the shaft of the electrode.

Another object of the invention is an electrosurgical handpiece manufactured by assembly of separable parts including a handle, collet, and nose piece, wherein the collet can be fixed to the handle without a gluing step.

According to one aspect of the invention, an electrosurgical handpiece comprises a handle and a nose piece for threaded engagement with the handle, together with a collet member which cooperates with the handle and nose piece for removably receiving and locking an electrosurgical electrode to the handle. The back end of the collet that grips the electrode shank is press-fitted into the bore of the handle in a manner that prevents the collet from being moved or turned during use by the surgeon. "Press-fitted" as used herein means an interference fit wherein the outer diameter of the collet back end exceeds that of the handle bore by at least 0.010 inches, and preferably by at least 0.016 inches. It turns out that this can not be achieved with a collet made of brass, as the brass, after stress has been applied and removed, often remains in its stressed position, so that the desired interference fit is lost after the collet has been pressed into the handle bore. In accordance with this aspect of the invention, the collet is made of a good electrically conductive material which has sufficient elasticity that it will return to its original unstressed condition when an applied stress is removed. A preferred material for the collet is beryllium-copper which exhibits the desired elasticity, sometimes referred to as spring properties. Such materials when subjected to the kind of stress required to press fit the collet into the handle bore will not become permanently set and if the collet were removed from the handle, no residual strain will be present. Such materials are well known and are available from many suppliers.

In accordance with another aspect of the invention, the front end of the collet is reconfigured with a single coaxial bore sized to accommodate a larger-sized shank. Preferably the collet has six slots instead of the usual four slots used in the known brass collet. It turns out that this allows the collet to receive and clamp not only the larger-sized shank but also a smaller-sized shank, provided that the collet is constituted of a good electrically conductive material which has sufficient elasticity that it will return to its original unstressed condition when an applied stress is removed. This result cannot be achieved with the known brass collet, because the clamping and removal of the smaller-sized electrode shank inevitably causes the collet bore to remain in its diminished condition and thus unable thereafter to accommodate the larger shank. With a collet of a material that is a good electrical conductor and possesses good elasticity, when the clamping pressure is removed, the collet is restored to its original unstressed condition and the collet can thus handle many insertions and removals of differently-sized electrodes without any ill effects.

In accordance with still another feature of the invention, the back end of the collet is provided with grooves. The advantage is that the outer diameter across the grooves of the collet back end can be increased to increase the interference and increase the holding power when the back end of the collet is press-fitted into the handle bore. The grooves provide sites for the displaced plastic to move into forming side-by-side plastic-metal circumferential regions that further ensure that no rotary movement of the collet with respect to the handle can occur.

As used herein, terms that define position are being related to the handpiece handle which possesses a longitudinal axis, and "front" means in a direction toward the electrode end of the handpiece whereas "back", "behind" or to the "rear" means in a direction away from the electrode end of the handpiece.

Since the novel electrosurgical handpiece construction allows the use of a collet which can be sized to accept multiple-sized electrodes, for example, the standard shank sizes of $1/16$ and $3/32$ inches, all standard electrodes can be employed to which can be attached the electrosurgical handpiece of the invention and which can thus removably receive any one of a family of electrodes capable of performing an electrosurgical function.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

The figures are not to the same scale.

DETAILED DESCRIPTION OF THE PREFERRED EMBODIMENTS

Figure 1:
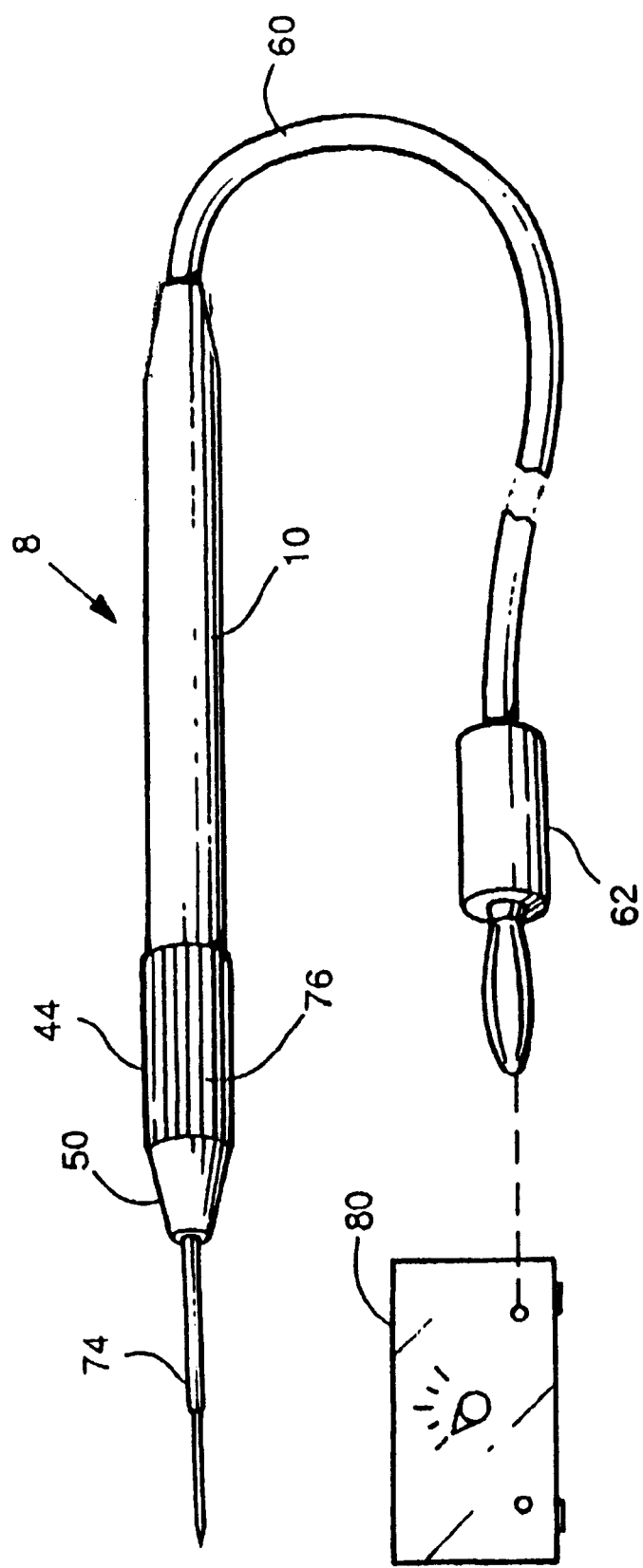
FIG. 1 is a perspective view of one form of an electrosurgical handpiece according to the invention shown with an electrode and shown schematically connected to an electrosurgical instrument for supply of electrosurgical currents.
Figure 2:
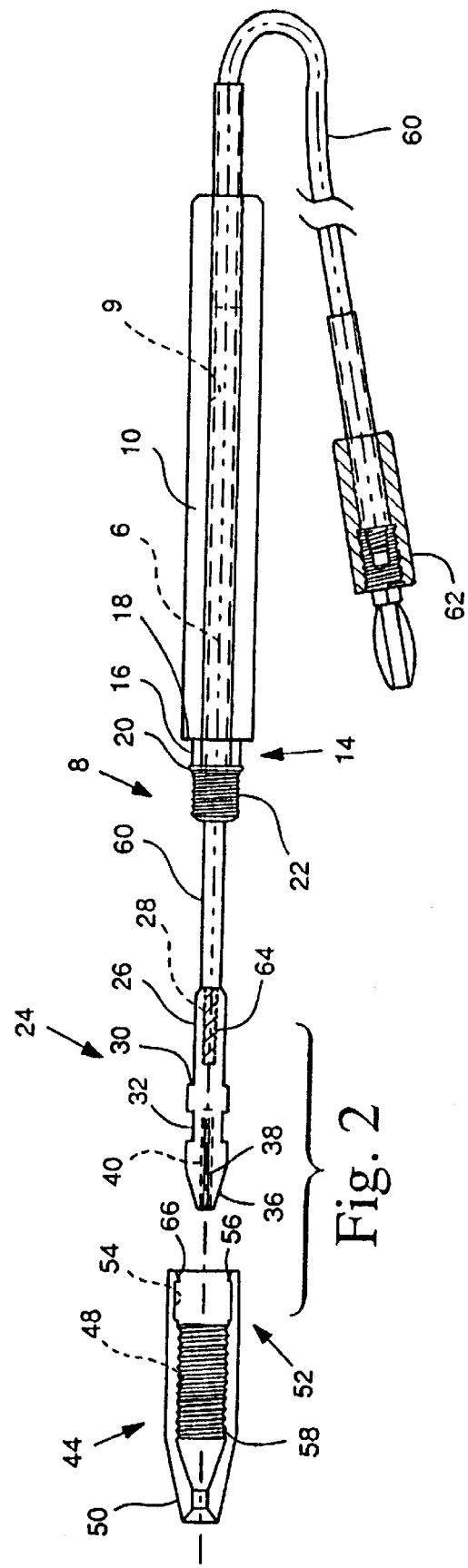
FIG. 2 is an exploded view of the electrosurgical handpiece shown in FIG. 1.
Figure 3:
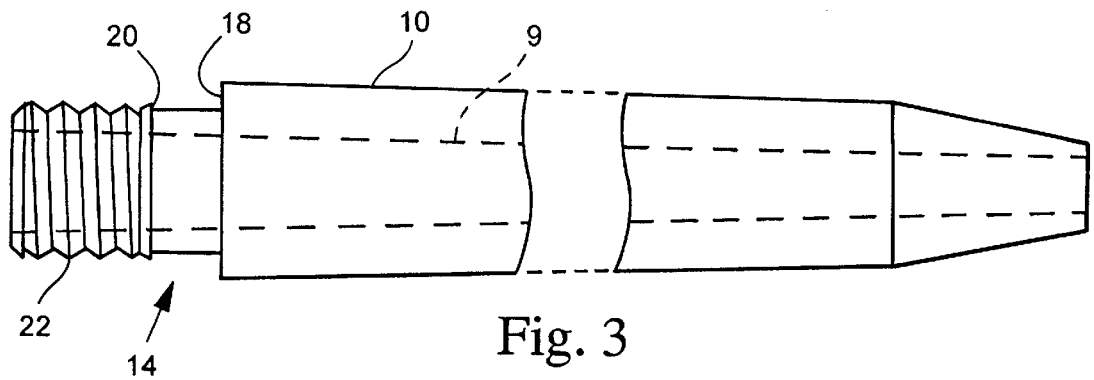
FIG. 3 illustrates in a side view one form of a handle used in the electrosurgical handpiece of the invention.
Figure 4:
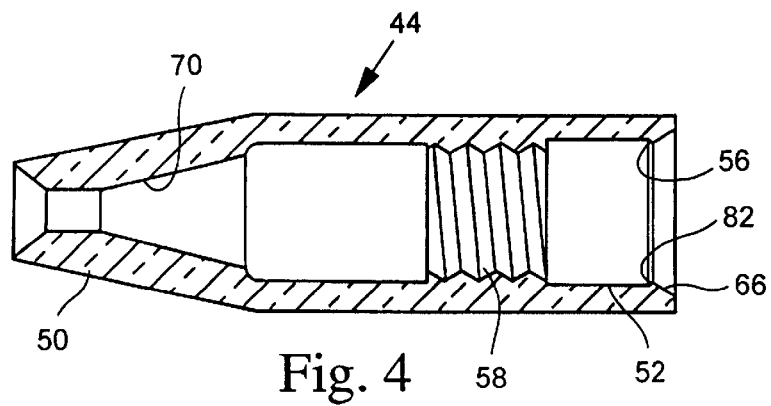
FIG. 4 illustrates in a side view one form of a nose piece used in the electrosurgical handpiece of the invention.
Figure 5:
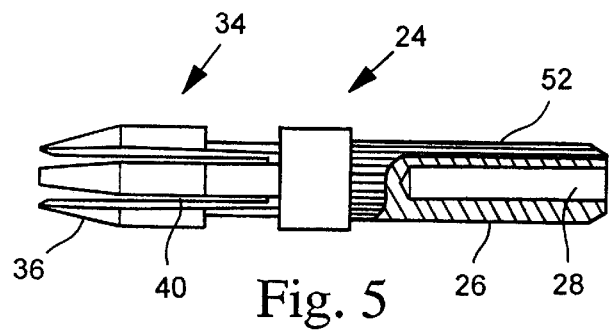
FIG. 5 illustrates in a partly cut-away, side view one form of a collet used in the electrosurgical handpiece of the invention.

FIGS. 1 and 2 show a preferred embodiment of an electrosurgical handpiece of the invention. The handpiece 8 comprises a straight, elongated, round handle 10 made, for example, of Delrin plastic, and provided with a bore 9 that extends throughout its length. A longitudinal axis is indicated by 6. At its left or front end is a reduced diameter cylindrical section that forms a first channeled region 14 with a cylindrical floor 16 and defined by a flanking shoulder 18 on the right and a flanking first ridge 20 on the left. The first ridge 20 is adjacent a forwardly projecting threaded portion 22.

A metal or otherwise electrically-conductive collet 24 has a rear cylindrical section 26 with a bore 28, located behind a shoulder 30, in turn behind a reduced diameter section 32 behind a collet head 34. The collet head 34 comprises at its left end jaws 36 formed by a tapered part that has six evenly-circumferentially-spaced slots 38 (FIG. 6) extending radially from the outside to a bore 40.

A nose piece is shown at 44, and comprises an electrically-insulating cylindrical member, for example, of Delrin, having a central bore 48. At its left, the nose piece 44 tapers down toward its bore to form a snout 50. At its right end, inside of the bore is located a second channeled region 52 with a cylindrical floor 54 flanked at its rear by a second ridge 56. Between the second channeled region 52 and the tapered front 50 is an internally threaded portion 58, matched to the threaded portion 22 on the handle.

The three parts 10, 24, and 44 making up the handpiece 8 are also shown in enlarged views in FIGS. 3–6.

The collet bore 40 is a single coaxial section sized to accommodate, for example, a $3/32$ inches shank; it is, for example, about 0.095 inches in diameter and extends about $1/3-1/2$ of the length of the collet. The back end 26 of the collet is provided with longitudinal grooves 52. The grooves 52 make it easier to press-fit the collet end 26 into the handle bore 9. Preferably the grooves take the form of a knurled surface As an example, which is not to be considered as limiting, for a bore 9 in a Delrin handle with an inner diameter of about 0.177–0.187 inches, the knurl is fabricated on a beryllium-copper collet rear end having a nominal diameter such that the widest part of the knurled end across the grooves is about 0.197–0.201 inches. In this case, the interference amounts to about 0.010–0.024 inches. The larger knurled end can still be force-fitted into the smaller bore 9 of the handpiece because the grooves formed during the knurling process will allow plastic displaced during the forcing process to flow into the grooves.

Prior to the press-fit step above described, an electrical cable 60 whose distal end is fitted with a banana plug 62 is threaded through the handle bore 9 and its free wire end soldered into the bore 28 at the rear of the collet 24, shown at 64 in FIG. 2. The cable with attached collet is then pulled to the right and the collet end press-fitted into the handle. Then, the nose piece 44 is fitted over the tapered collet end 34 and over the threaded portion 22 until the latter is engaged by the threaded portion 58 on the nose piece, and the nose piece piece 44 is then rotated CW to threadingly engage the mating threaded portions 22, 58. After about 8–10 turns, the second ridge 56 at the rear of the nose piece engages the first ridge 20 on the handle front end. At that point, the nose piece, with ordinary force, cannot be rotated any further.

As described in the referenced patent, the ridge 56 has a bevelled rear end 66, and is configured and sized relative to the size of the ridge 20 that a much stronger force will force the second ridge 56 over the first ridge 20 and into the first channeled region 14. Simultaneously, the first ridge 20 will then be located in the second channeled region 52. Both channeled regions 14, 52 are configured and sized such that there is clearance between the innermost ridge surface and the respective channeled region floor in which it is now positioned so that the nose piece rotates freely. The length of each channeled region 14, 52, in the axial direction is such that the nose piece 44 can then be rotated at least an additional 6–10 turns such that, before it has reached the end of its travel, all interior tapered section 70 will engage the tapered front of the collet 24 thereby forcing inward the collet jaws 36 defined by the slits 38. An electrode 74 whose shaft is inserted in the bore 40 of the collet will then be tightly held by the collet jaws 36 which will prevent further rotation of the nose piece 44. In the assembled condition, the electrically-insulating nose piece 44 covers the metal collet 24 except for the working end of the electrode 74 which projects forwardly from the front end of the handpiece. To ease rotation of the nose piece 44, the surface may be knurled as shown at 76. The bevelled rear end of the collet assists in the press-fitting operation.

When the plug 62 is plugged into a conventional electrosurgical instrument 80 and the instrument activated, electrosurgical currents will flow from the instrument via the cable 60 to the handpiece 8, and via the collet 24 to the electrode 74.

When it is desired to remove or replace the electrode, the nose piece 44 is rotated CCW. Sufficient rotation of the nose piece 44 is allowed by the axial length of the channeled regions to allow the natural elasticity of the metal of the collet jaws 72 to relax to release the electrode which can then be withdrawn from the handpiece. However, further CCW rotation of the nose piece 44 which would allow it to be detached from the handle is prevented by the non-bevelled side 82 of the second ridge 56 which engages the rear side of the first ridge 20. Thus, the nose piece has sufficient room to rotate enough turns to allow an electrode to be tightly or loosely held and removable from the handpiece, but the nose piece cannot be detached from the handpiece because of the interfering ridges 20, 56.

What is not shown in the drawings are the standard switches that can be added to the handpiece so that the electrode can be turned on and off by the surgeon using the handpiece switches. Also not shown is the standard footswitch which also plugs into the electrosurgical instrument 80 for operating the handpiece.

The particular electrode 74 shown in FIG. 1 has an active or working end in the form of a needle. Other shapes are of course possible, such as wire loops and balls.

While the parts of the. electrosurgical handpiece, made up of metal and Delrin, are auto-clavable, the device is sufficiently simple that it can be manufactured at very low cost with a less expensive plastic and thus can be made disposable.

As described above, the collet 24 must be constituted of an electrically conductive metal that has a certain amount of elasticity or spring force, meaning that, when a stress is removed, it will tend to return to its original dimensions. This property allows it to be force fitted into the plastic bore without breaking the plastic body and yet will be solidly retained in a fixed and immovable position with respect to the handle. It is the same property that enables the larger opening 40 between the collet jaws—sized to receive the larger-sized electrode shank—to be clamped onto the smaller-sized shank and yet when released by the nose piece will allow the jaws to spring back to their original opening so that they will again be able to receive the larger-sized shank. This result could not be obtained with the brass collet used in the known handpiece. However, it has been found that beryllium-copper is well suited as the collet material for this purpose. A typical beryllium-copper alloy available commercially contains about 2% beryllium. Such an alloy is also known for its high electrical conductivity and its high endurance limit, which is the property that makes it suitable for use in springs. While other high elasticity materials are also suitable for the collet material of the invention, such as titanium and hardened stainless steel, the combination of high electrical conductivity, high endurance, and high elasticity makes beryllium-copper the preferred material. The rear end of the collet is bevelled to assist in the press-fitting operation.

Other plastics with similar properties to the Delrin may also be suitable, but the latter is preferred because it has a certain degree of softness, which causes the knurls to dig into it to increase retentivity.

Another feature of significance to the ability of the collet to accommodate different-sized shanks is the presence of six slots 38 with slot widths (circumferential spacing between adjacent jaws 36) varying between about 0.018–0.025 inches. This range of slot clearances allows the jaws 36 from its nominal unstressed condition to close over a wider range of bore diameters which enables the jaws to clamp onto the different-sized shanks before the jaws engage and prevent further closure.

Figure 6:
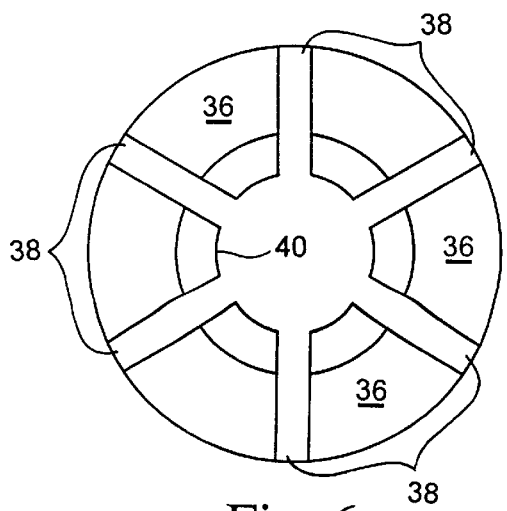
FIG. 6 is an enlarged front view of the collet of FIG. 5.
Figure 7:
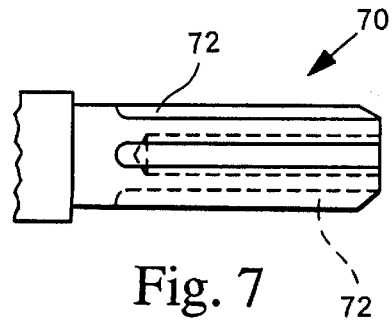
FIG. 7 shows a modification of the back end of a collet useful in the invention.

FIG. 6 shows a variation of the collet back end 70 in which the knurls have been replaced by deeper axially-parallel grooves 72 which provides more clearance room to accommodate displaced plastic from the handle bore walls as the collet back end is press-fitted into the handle bore 9.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical handpiece comprising:

an elongated handle member having a longitudinal axis and having at a first end a first threaded portion for receiving a nose piece, first means for removably receiving and holding an electrode, said first means comprising a collet and being positioned on the handle member at its first end such that when an electrode is mounted on and gripped by the first means it projects generally parallel to the longitudinal axis in a direction frontward of the handle member, an electrode connector connected to the first means, a nose piece having a second threaded portion for threaded engagement with the first threaded portion and configured such that, when rotated while in threaded engagement with the first threaded portion of the handle member, the nose piece functions to cause the first means to tighten and to loosen its grip on the electrode, the first threaded portion of the handle member having a bore of a given inside diameter extending rearwardly, the collet having at its end remote from the nose piece a generally cylindrical section whose widest dimension transverse to the axis exceeds the given inside diameter of the handle member bore, said collet remote end being press-fitted into the handle member bore, said collet remote end and said handle member bore being dimensioned such that the press-fitted collet remains in a fixed position with respect to the handle member.

2. An electrosurgical handpiece as claimed in claim 1, wherein the first means comprises a collet having jaws.

3. An electrosurgical handpiece as claimed in claim 2, wherein the nose piece has a tapered portion for engaging the collet jaws to close and allow them to open when rotated.

4. An electrosurgical handpiece as claimed in claim 2, wherein the collet is constituted of an electrically-conductive metal having sufficient elasticity to allow any stressed collet parts to return to their original unstressed condition when the stress is removed.

5. An electrosurgical handpiece as claimed in claim 1, wherein the handle member is of plastic and the generally cylindrical section of the collet comprises grooves.

6. An electrosurgical handpiece as claimed in claim 1, wherein the handle member is of plastic and the generally cylindrical section of the collet is knurled.

7. An electrosurgical handpiece as claimed in claim 6, wherein the widest dimension of the knurled section transverse to the handle axis is at least about 0.010 inches larger than the inside diameter of the handle member bore.

8. An electrosurgical handpiece as claimed in claim 1, wherein the collet is constituted of beryllium-copper.

9. An electrosurgical handpiece comprising:
   an elongated handle member having a longitudinal axis and having at a first end a first threaded portion for receiving a nose piece,
   first means for removably receiving and holding an electrode having a shank, said first means comprising a collet having jaws surrounding a bore and being positioned on the handle member at its first end such that when an electrode shank is inserted in the collet bore and gripped by the collet jaws the electrode projects generally parallel to the longitudinal axis in a direction frontward of the handle member,
   an electrode connector connected to the first means,
   a nose piece having a second threaded portion for threaded engagement with the first threaded portion and configured such that, when rotated while in threaded engagement with the first threaded portion of the handle member, the nose piece functions to apply pressure to the collet to cause the collet jaws to tighten its grip on the electrode shank,
   the collet bore having a lateral dimension sufficiently wide to receive multiple-sized electrode shanks, the collet jaws being sufficiently circumferentially spaced apart so as to close in clamping engagement with multiple-sized electrode shanks, the collet being constituted of an electrically-conductive metal having sufficient elasticity to allow closed collet jaws to return to their original unstressed condition when the pressure is removed.

10. An electrosurgical handpiece as claimed in claim 9, wherein the nose piece has a tapered portion for engaging the collet jaws to close and allow them to open when rotated.

11. An electrosurgical handpiece as claimed in claim 9, wherein the collet bore has an inside dimension to accommodate a 3/32 inches shank of an electrode.

12. An electrosurgical handpiece as claimed in claim 9, wherein the collet has six jaws.

13. An electrosurgical handpiece as claimed in claim 12, wherein the collet jaws are circumferentially-spaced apart by slots having a circumferential width between about 0.018–0.025 inches.

14. An electrosurgical handpiece as claimed in claim 9, wherein the collet is constituted of beryllium-copper.

15. An electrosurgical handpiece as claimed in claim 9, further comprising means on the nose piece and handle member and functioning to automatically lock the nose piece to the handle member, in a position overlying the collet, when the nose piece and handle member are in threaded engagement yet still allow a limited amount of rotation of the nose piece relative to the handle member so it can carry out its function of causing the collet to tighten and to loosen its grip on the electrode, said means comprising a first ridge on the handle member interfering with a second ridge on the nose piece and allowing the second ridge to ride over the first ridge only upon the application of excessive turning force applied to the nose piece relative to the handle member.

16. An electrosurgical handpiece as claimed in claim 15, wherein the handle member comprises a first channeled region adjacent and to the rear of the first ridge for receiving with clearance the second ridge when it rides over the first ridge, and the nose piece comprises a second channeled region adjacent and in front of the second ridge for receiving with clearance the first ridge when it rides over the second ridge.

17. In combination, the electrosurgical handpiece as claimed in claim 1 and an electrode having a shank sized to fit within the collet bore.

18. In combination, the electrosurgical handpiece as claimed in claim 9 and at least two electrodes having different-sized shanks sized to fit within the collet bore when in its unstressed condition.

* * * * *